(12) United States Patent
Hunter

(10) Patent No.: US 6,511,319 B1
(45) Date of Patent: Jan. 28, 2003

(54) DENTAL PROPHYLAXIS HANDPIECE

(76) Inventor: Frank Hunter, 93 Ocen View Drive, Terrigal, N.S.W., 2260 (AU)

( * ) Notice: Subject to any disclaimer, the term of this patent is extended or adjusted under 35 U.S.C. 154(b) by 0 days.

(21) Appl. No.: 09/719,414

(22) PCT Filed: Jun. 9, 1999

(86) PCT No.: PCT/AU99/00446

§ 371 (c)(1), (2), (4) Date: Feb. 28, 2001

(87) PCT Pub. No.: WO99/63905

PCT Pub. Date: Dec. 16, 1999

(30) Foreign Application Priority Data

Jun. 10, 1998 (AU) .............................................. PP4019

(51) Int. Cl.$^7$ ................................................. A61C 3/03
(52) U.S. Cl. ........................................ 433/122; 433/125
(58) Field of Search ......................... 433/122 OR, 124, 433/125 R, 123, 118

(56) References Cited

U.S. PATENT DOCUMENTS

| | | | | |
|---|---|---|---|---|
| 3,552,022 A | * | 1/1971 | Axelsson | 433/122 |
| 3,939,599 A | * | 2/1976 | Henry et al. | 433/125 |
| 4,183,140 A | * | 1/1980 | Rieselman | 433/125 |
| 4,341,519 A | * | 7/1982 | Kuhn | 433/122 |
| 4,460,341 A | * | 7/1984 | Nakaishi | 433/122 |
| 4,534,733 A | * | 8/1985 | Seigneurin | 433/122 |
| 4,976,625 A | * | 12/1990 | Weissman | 433/118 |
| 5,071,348 A | * | 12/1991 | Woog | 433/118 |
| 5,099,536 A | * | 3/1992 | Hirabayashi | 433/125 |
| 5,340,310 A | * | 8/1994 | Bifulk | 433/123 |
| 5,454,718 A | | 10/1995 | Strohmaier | 433/122 |
| 5,749,728 A | * | 5/1998 | Bailey | 433/125 |

FOREIGN PATENT DOCUMENTS

| | | |
|---|---|---|
| CH | 688 261 | 7/1997 |
| DE | 42 18 683 | 12/1993 |
| DE | 195 09 840 | 3/1996 |
| EP | 0 064 871 | 11/1982 |
| WO | WO 90/00885 | 2/1990 |
| WO | WO 97/39695 | 10/1997 |

* cited by examiner

*Primary Examiner*—John J. Wilson
(74) *Attorney, Agent, or Firm*—Christie, Parker & Hale, LLP

(57) ABSTRACT

A handpiece is provided. The handpiece comprises a shaft one end of which includes a connection means in the form of a shank to accept an aperture in a dental handpiece drive, the other end of the shaft includes a pin with a central longitudinal axis offset from the central longitudinal axis of the shaft. Bearings are disposed about the shaft at either end so as to support the shaft in a casing which extends to encompass the shaft, the casing including a portion at one end which is enlarged to accept the dental handpiece drive and at the other end a housing into which the pin protrudes. The housing is adapted to retain a member comprising a mounting component and a head, which head is disposed outside of the housing and to permit the pin to engage in a groove in the member in a manner such that operation of the dental handpiece drive causes the shaft to rotate which in turn imparts an oscillating arcuate motion to the member including the head. Usually the head will comprise an array of bristles for application to dental tissues.

61 Claims, 8 Drawing Sheets

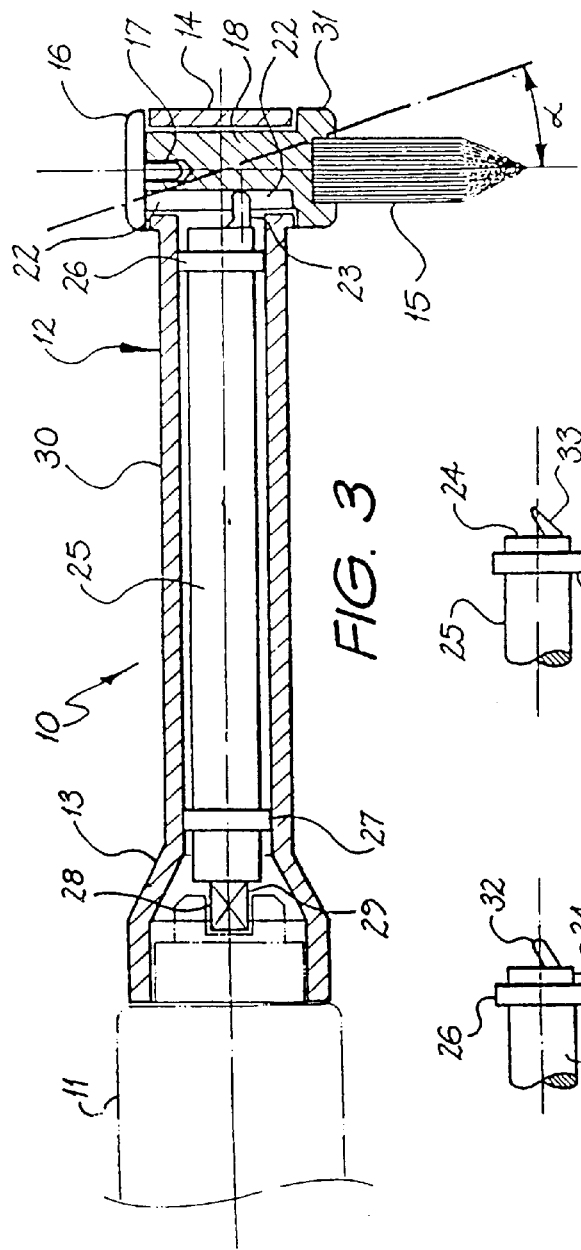

DENTAL PROPHYLAXIS HANDPIECE

CROSS-REFERENCE TO RELATED APPLICATION

This application claims priority of PCT International Application Number PCT/AU99/00446 filed on Jun. 9, 1999, and Australia patent Application No. PP4019, filed on Jun. 10, 1998.

TECHNICAL FIELD

This invention relates to an apparatus for use in the improvement of oral health especially in dental hygiene and more particularly to a device which may be used by dentists, hygienists and other personnel in relation to the prevention and treatment of dental diseases.

BACKGROUND ART

Dental diseases include both dental caries (tooth decay) and a group of gum diseases, collectively referred to as "periodontal diseases". The most common aetiological factor or causative agent in both tooth decay and gum diseases is the presence of dental plaque.

Historically, tooth decay was the most common of all human diseases effecting man throughout the world. Tooth decay is the result of demineralisation of firstly, the outer layer of tooth enamel and then, subsequently, by a similar demineralisation of the inner body of dentine within the tooth. This demineralisation is brought about by an acid attack on the tooth surface. This acid is most commonly derived from acidogenic activity of the microbiological flora within the plaque mass, as the flora metabolise the carbohydrate content of that same plaque mass, or other sugar compounds within the diet of the host.

However, since the introduction of fluoride into water supplies, toothpastes, drinks, foods, tablets, special solutions and gels applied by the dental professional and through other avenues, the fluoride content of human tooth enamel has increased to the point where many teeth are now much more resistant to acid attack and so dental caries (tooth decay) has declined in significance and incidence throughout the world.

Nevertheless, this relative "strengthening" of human tooth enamel has not addressed the main cause of dental caries, namely that of the presence of dental plaque. Thus, more recently there has been an increase in tooth decay on those tooth surfaces which are not covered by human tooth enamel, such as the roots of the tooth.

Moreover, the gums which comprise soft gingival tissue and the collection of periodontal fibres, connective tissue, cementum, periosteum and bone, commonly referred to as the "periodontal apparatus" and which collectively support and retain the tooth in the mouth, also respond to the presence of dental plaque, to the point where this entire mechanism may break down and the tooth is lost.

Thus, periodontal or gum diseases themselves have now become amongst the most common of all diseases affecting humans throughout the world today and are now the major cause of adult tooth loss.

Ironically the most common cause of both tooth decay and gum diseases is dental plaque. The diagnosis, treatment and management of these two major dental diseases is within the exclusive domain and responsibility of the dental profession.

However, the control of the primary causative agent, dental plaque, is such an important and/or arduous task, that the profession has introduced a speciality and auxiliary discipline within the profession, called "Dental Hygienists and/or Therapists". An important task of the dental clinician is to remove this damaging substance and to instruct the individual patient how best they can attain control of this menace.

However, the clinical challenge confronting the dentist, hygienist, therapist or other dental clinicians is exacerbated by the limitations of the tools available to them to perform these tasks.

Clearly, the incidence and resultant damage to human health caused by dental plaque would suggest that the profession is failing to address their responsibility in this area and, further, that the tools available to the professional and the patient are inadequate.

The present inventor has thoroughly researched the derivation, accumulation and application of dental plaque. As a direct result of this research, the inventor has designed a system that addresses the very basic requirements of plaque control and this information, technology and appliances form the basis of this patent application.

Dental Diseases

The two most common and significant of all dental diseases are:

1. Tooth decay—"Dental Caries"
2. Gum diseases—"Periodontal Diseases"

Aetiology

The common primary causative agent to both these diseases is dental plaque.

Sites

1. Local

It is estimated that over 75% of dental diseases commence in between the teeth in the area referred to as the "interproximal" region and, more specifically and in the classic model, in an area extending from the point of contact between adjacent teeth to the gingival attachment level at the cemento-enamel junction, where the crown of the tooth meets the root of that tooth. This area may be referred to as the "embrasure triangle".

This site is the most important of all dental disease sites, since it contains both hard (tooth) and soft (gum) tissues and so plaque retention in this area may give rise to both tooth decay and gum disease. This area may be referred to as the "hot spot" of dental diseases.

The next most significant site for dental diseases, especially periodontal diseases is around the gum line on either the outer ("facial", "labial" or "buccal") or inner ("atral", "palatal" or "lingual") surfaces of each tooth or in the gingival sulcus. This factor may be exacerbated by angled, rotated, tilted, crossed or crowded teeth, all of which facilitate the retention of dental plaque and make its removal more difficult.

The next most significant site in the prevention and treatment of dental caries are the deep fissures, which may occupy an area of the top, biting or "occlusal" surface of the tooth. In these areas, small particles of food and/or plaque may be pushed into these fissures and be difficult to remove with conventional devices. Depending upon the local anatomy, these fissures may also represent a very thin layer of tooth enamel and so be more vulnerable to acid attack.

Similar to the fissures, the next most significant site for dental caries to occur, may be in the anatomical anomalies referred to as "pits". These defects in the tooth enamel are often deep and may occur on either the outer ("facial", "labial" or "buccal") or inner ("lingual", "atrial" or "palatal") surfaces of the tooth.

2. Regional

The above sites identify localised areas on or around the tooth and gum surfaces which are prone to most dental disease attack due to the accumulation and retention of dental plaque. It should be noted that dental plaque is generated daily within a normally healthy mouth. It is a sticky, viscous or gelatinous mass that may grow, unless removed effectively.

However, if dental plaque is let accumulate for more than one day, it may calcify to form calculus (sometimes called "tartar"). This is a harder, chalky mass which binds to the tooth surface and is much more difficult to remove than its softer precursor, dental plaque.

If left to grow and accumulate on the tooth surface, this calculus, being rough attracts more plaque around its mass and so the process continues, the calculus gets larger and more plaque accumulates around the tooth and/or gum surfaces.

A common source of the calcium necessary for this process to occur is the calcium ions, resident within saliva. Thus, at sites where the saliva enters the mouth and subsequent accumulation of calculus takes place, the risk of dental diseases commencing is increased. The most common sites so described are the inner surfaces of the lower anterior teeth (lingual surfaces of lower incisors) and the outer surfaces of the upper posterior teeth (buccal surfaces of upper molars). Any other site of surface roughness, which retains plaque, such as defective restorations or anatomical anomalies, also represents a disease risk site.

The present inventor has recognised that there exists a need for an effective device for the maintenance of oral hygiene and in particular, the maintenance of good periodontal hygiene.

SUMMARY OF THE INVENTION

Accordingly, the present invention consists in a dental prophylaxis handpiece comprising a shaft one end of which includes a connection means to accept a dental handpiece drive, the other end of the shaft including a pin with a longitudinal axis either parallel or at an angle to but not on the longitudinal axis of the shaft, one or more bearings disposed about the shaft so as to support the shaft in a casing which extends to encompass the shaft, the casing including a portion at one end to accept the dental handpiece drive and at the other end a housing into which the pin protrudes, the housing being adapted to retain a member comprising a mounting component and a head, which head is disposed outside of the housing and is for application to dental tissues, and to permit the pin to engage in a groove in the member in a manner such that operation of the dental handpiece drive causes the shaft to rotate which in turn imparts an oscillating arcuate motion to the member including the head.

In another aspect, the present invention further consists in an electrically driven handpiece comprising a shaft one end of which is adapted to drivingly connect to an electric motor, the other end of the shaft including a pin with a longitudinal axis either parallel or at an angle to but not on the longitudinal axis of the shaft, one or more bearings disposed about the shaft so as to support the shaft in a casing which extends to encompass the shaft, the casing including a portion at one end to contain the electric motor and a source of power for the motor and at the other end a housing into which the pin protrudes, the housing being adapted to retain a member comprising a mounting component and a head, which head is disposed outside of the housing and is for application to dental tissues, and to permit the pin to engage in a groove in the member in a manner such that operation of the electric motor causes the shaft to rotate which in turn imparts an oscillating arcuate motion to the member including the head.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Oral Hygiene—In Perspective

1. Inter-Proximal

The inter-proximal region and, in particular, the embrasure triangle, thus represents the most important site in the prophylaxis, or prevention of dental diseases.

However, the motion of conventional "prophylaxis handpieces" and the shape of conventional "prophylaxis heads" are not capable of penetrating this confined and uniquely shaped area. Moreover, even if these devices are forced to penetrate this disease hot spot, their very continuous circular or rotary motion and poor head design may bring about a burning, burnishing and general danage to the local soft tissue, namely the gingival crest.

It should also be noted that the continuous circular or rotary motion of current devices imparts a centrifugal force which tends to propel plaque, blood, puss, bacteria, viruses, pathogens, saliva, oral debris and other matter in a perpendicular direction tangential to the working surface of the rotating head to cause a "splatter" and spread of infectious material and all other matter around the immediate working environment of the device and thereby expose disease transfer risks to all people within that environment.

Not surprisingly, then the profession is not able to address the very demands placed upon it by their responsibility to remove this menace and thereby prevent what is the most common disease process affecting human health throughout the world today.

Moreover, the continuous circular or rotary motion of current devices invites the device to engage in resistance of tissue surfaces which causes the device to "skid" off these surfaces and "run off" in an uncontrolled direction. Thus the operator must continuously "fight" this dangerous tendency- a factor which causes much frustration, fatigue and fury, let alone exposing the tissue to unnecessary damage.

Clearly, what is needed is a special, purpose built device which is not only capable of penetrating this disease hot spot, but which entertains such a motion that will effectively remove plaque but not cause damage to the tissue, is tissue friendly to both hard and soft tissues, promotes healing and which will actually massage any affected soft tissue back to a state of clinical health whilst not causing 'splatter' or spread of any pathogens or infectious matter.

The present inventor believes that the dental prophylaxis handpiece now provided meets this need.

2. Gum Line Surfaces

The next most essential ingredient in such an oral hygiene device is that it can effectively clean the gum line of all teeth, again, without causing damage to either the hard or soft tissues and that it should be capable of massaging any affected soft tissue back to clinical health.

The dental prophylaxis handpiece of the invention has been so designed to achieve both inter-proximal hygiene and gum surface debridement simultaneously, to not cause damage to either hard or soft tissue and to massage the soft tissue, all at the same time. This has been achieved by the selection of unique head designs and a sensitive arcuate motion delivered to that head by the unique mechanical design of the handpiece.

Moreover, "splatter" from conventional prophylaxis handpieces has caused so much concern amongst oral health care professionals, that some manufacturers have tried to develop "splatter-free" pastes and have designed special features within the rotating rubber cups to minimise this menacing effect and health care risk, resident within these devices.

In an attempt to combat the spread of infectious material caused by rotating devices, the oral health care profession has been forced to wear protective glasses, face masks, rubber gloves and other expressly protective utilities. This causes financial and enviromental burden which may be reduced through the use of the present invention.

3. Occlusal Surface Fissures

The occlusal surfaces, together with their deep fissures are difficult to clean with conventional rubber cups, bristle brushes and the common circular motion as is currently available through regular dental handpieces.

The present invention has been proven to be more efficient in terms of time and extent of debridement it performs in these often difficult to get to areas. Further, the preparation of the fissures for the preventive procedure referred to as "fissure sealing" is much more enhanced by the use of the present invention. Again, this feature is due to the exclusive design of the heads and the arcuate motion delivered to those heads by this handpiece.

4. Coronal Pits

Indeed most coronal abnormalities are difficult to clean, when using conventional prophylaxis handpieces. Especially, rubber cups are not capable of engaging these defects.

The unique head design and arcuate motion of the heads of the present invention has shown to be most effective in the debridement of these dental defects.

5. Intervention

The above features refer to prevention of the disease process. However, since dental diseases are often already under way in many patient's mouths, the need for effective intervention is obvious. Unfortunately, the conventional prophylaxis handpieces are not capable of performing this important task, without considerable risk of further damage being imposed upon the very tissue we are trying to treat. This device performs this task as well.

The shaft of the handpiece may be circular or multi-sided in cross-sections. Preferably, the shaft is circular in cross-section.

In the event that a multi-sided shaft is chosen, it is important that such a shaft generally include one or more portions which are circular in section to allow for the disposition of one or more bearings to support the shaft in the casing. Alternatively, a ball bearing with a suitably shaped inner surface to correspond with the cross sectional shape of the shaft may be used.

Generally, irrespective of whether the shaft is circular or multi-sided in cross-section, two bearings will be used to support the shaft, a first bearing disposed about the shaft proximate the one end of the shaft and the second bearing about the shaft proximate the other end of the shaft.

For reasons of durability, it is desirable that the shaft is made of metal, although plastics materials may be used. The person skilled in the art would recognise that a variety of metals may be used including stainless steel, mild steel and other alloys.

Similarly, usually the one or more bearings will be made of metal. although plastics materials could be used. The material of construction and the design of the bearings need to be consistent with amongst other things, the rotational speed of the shaft. Examples of suitable bearings are journal bearings, roller bearings and ball bearings.

The connection means may comprise a slot in a face of the one end of the shaft. This slot may be multi-sided in cross-section.

Alternatively, the connection means may comprise a shank which projects out of a face of the one end of the shaft. This shank may be multi-sided in cross-section.

The nature of the connection means will be determined by the kind of dental handpiece drive used. To allow for maximum utility of the handpiece of the invention, the slot is arrayed to accept a drive from those drives that are used in the dental profession. These drives include handpiece drives such as Doriot. E-type, Borden and mid-west including that imparted by a piece intermediate between the dental motor drive and the disposable handpiece commonly referred to as a "nose cone". Note, however, that the shaft may be dimensioned or configured in any way to accept any drive.

Furthermore, the handpiece drive may rotate clockwise or anticlockwise at conventional speeds of 0–40,000 rpm. Gearing may be included so as to reduce the final rotation speed to 0–5,000 rpm from 0–40,000 rpm.

In the electrically driven handpiece aspect of the invention, the shaft is adapted to drivingly connect to an electric motor. This may occur by a variety of means including direct coupling to the shaft of the electric motor or through an appropriate combination of gears mounted on each shaft. The person skilled in the art will also recognise that a common shaft may used. In this embodiment, a single shaft projects out of the electric motor.

The other end of the shaft includes a pin having a longitudinal axis which is either parallel or at an angle to but not on the longitudinal axis of the shaft. Preferably the pin is mounted on a face of the other end of the shaft, Although dependent on the diameter of the shaft, preferably the pin will be about 1–3 mm from the centre of the shaft, most preferably about 2 mm. Preferably the pin will have a width of between about 1 and 2 mm, most preferably about 1.5 mm. Alternatively, the pin may be tapered with the widest dimension on the shaft.

A casing is used to contain the shaft and to provide a mounting for the bearing(s). The casing may be made from a variety of plastics materials and metals. In general terms, casings formed from metal, such as aluminium and its alloys, stainless steel and the like will be more durable and are capable of sterilisation by accepted means thereby allowing for reuse. Likewise, single use or disposable handpieces, when required, may be formed from less durable plastics material such as polypropylene, polycarbonates, or combinations thereof or any other plastic resin material.

To assist in assembly, the casing may be formed from two halves. In such an embodiment, the halves are preferably formed in longitudinally extending portions. The half portions will have suitable mating surfaces with means being provided to join the halves together. Such means may include one or more fasteners which pass through opening(s) in one half to mate with suitable receptacle(s) in the other half. For example, the fasteners may be screws with the receptacle(s) having corresponding portions to accept the screw thread.

Alternatively, the casing may be formed in one piece. For example, when made from synthetic plastics material, the casing may be injection or blow moulded.

In the electrically driven handpiece aspect, the casing also contains the electric motor and power source. For convenience, the power source may be one or more batteries, optionally rechargeable. Alternatively, the power source may comprise a suitable plug or socket for connection to a domestic power supply. In any event, preferably a switch will be mounted in or on the casing to allow for power to be supplied to the electic motor as required.

In one embodiment, the casing may be enlarged at the one end so as to more easily accept the dental handpiece drive. The portion of the casing between the enlarged section and the housing may be substantially cylindrical in shape, tapered or contra-angled. If tapered, the casing will taper inwardly from the enlarged section towards the housing. Note that the taper may be over a full or a part length of the casing. When part tapered, a substantially cylindrical portion of the casing will be adjacent the housing.

When the casing is contra-angled, generally a portion of the casing adjacent the enlarged section will be substantially cylindrical or tapered with the portion of the casing adjacent the housing contra-angled. In this context, "contra-angled" refers to the acute angle formed between the longitudinal axis of the substantially cylindrical portion of the casing and the longitudinal axis of the contra-angled portion of the casing. Such a contra-angle is desirable as existing dental devices utilise this feature.

It follows that in embodiments that include a contra-angled casing, the shaft will comprise two shaft components. A first shaft component will include the connection means at one end and a first coupling means at the other end. The first shaft component will extend along the longitudinal axis of the substantially cylindrical portion. A second shaft component will include a second coupling means at one end and the pin at the other end. The second shaft component will extend along the longitudinal axis of the contra-angled portion.

Both the first and the second component shafts will be mounted in the casing on one or more bearings as appropriate in a manner such that the first and the second coupling means are in driving engagement. Similarly the shafts may engage any number of gears in order to reduce its final rotational speed from 0–40,000 rpm to 0–5.000 rpm or any speed in between 0–40,000 rpm.

Although the person skilled in the art will recognise that a variety of coupling means may be used, one preferred coupling means is the combination of a crown gear and a pinion gear. In this invention, the first coupling means and the second coupling means could be a combination of either gear.

It is also desirable that the casing be provided with a means on an outer surface thereof to enhance control and/or comfort of the handpiece. Such means may comprise flattened portions to form a casing having a polygonal cross-section or sunken grip points. Alternatively, raised portions may be provided on the outer surface of the casing for the same purpose.

The handpiece includes a housing into which the pin protrudes. This housing is adapted to retain a member which comprises a mounting component and a head. The head is disposed outside of the housing and is for application to dental tissue.

In protruding into the housing, the pin must be engageable with a groove in the mounting component such that operation of the dental handpiece drive causes the shaft to rotate which in turn imparts an oscillating arcuate motion to the member, including the head. The arcuate angle will usually be up to 90°, preferably up to about 45°.

Generally, the housing will be substantially cylindrical in shape. Preferably, the longitudinal axis of the housing is at an angle of between about 90° and about 125° with respect to the longitudinal access of the shaft. For ease of construction, the housing will usually be formed as an integral part of the casing.

The member, including the head, retained by the housing comprises a mounting component and a head. Preferably the mounting component is substantially cylindrical and is in sliding contact with an inner surface of the housing. Alternatively, the mounting component may have one or more bearing surfaces to engage an inner surface of the housing.

In a preferred embodiment, the pin engages in a groove which is disposed in the mounting component such that the groove extends in a plane through the longitudinal axis of the member. The groove may extend completely or partially along the member.

In another embodiment, the groove may extend in a plane through the transverse axis of the member. Again, the groove may extend completely or partially along the member.

In an embodiment wherein the mounting component is substantially cylindrical, preferably it is in frictional engagement with a surface of the housing so as to retain the member therein. This may be achieved by providing a rim formed on an upper surface of the mounting component, the rim bearing on an upper edge of the housing so as to retain the member in the housing.

Alternatively, the member may include a second groove in the mounting component, the groove extending transversely to engage a second pin disposed within the housing so as to retain the member therein.

Similarly any other means of retaining the member within the housing may be used, such as a latch or any other effective retention piece both in the member or the housing.

The present inventor has discovered that the width of the groove and the angles of its walls, together with the eccentricity of the pin directly affect the amplitude of the arc of the member, including the head particularly under light loading. By "eccentricity of the pin" it is meant the extent to which the pin is positioned away from the longitudinal axis of the shaft. However, when the head is loaded whilst in use in a narrow or tight space, this amplitude reduces considerably. This difference in amplitude of the arcuate oscillation is referred to in this specification as the "tidal load slap" this factor has proven to be an advantage, especially when dealing with the wide variations in the degree of dental crowding, gaps between teeth and the degree of massage necessary to effectively treat some gum conditions. This degree of tidal load slap also acts as a buffer to reduce any aggressive movement of the head and thereby minimise damage to the dental tissue.

Accordingly, it is preferred that the external width of the groove is about from 1 mm to 3 mm. Most preferably about 2 mm.

Similarly, the internal width of the groove is preferably about 0.5 mm to 2 mm, most preferably about 1 mm.

The depth of the groove is preferably about 1 mm to 3 mm, most preferably about 2 mm. In some embodiments, it may extend within the mounting component to be continuous with a hollow central portion formed therein.

The groove may have parallel sides or be flared internally or externally. In this context flaring internally refers to embodiments where the external width of a groove is less than the internal width of a groove. Similarly, flaring externally refers to embodiments where the external width of a groove is greater than the internal width of a groove.

Alternatively, the pin may be tapered and the groove angled to form a V-shape so that the internal surface of the groove engages the tapered surface of the pin at all times.

It will be appreciated that the mounting component and head may be integrally formed, formed separately and permanently joined or formed separately and separably joined. The advantage in providing a separably joinable head is that it allows for ready replacement.

As previously mentioned, the member comprises a mounting component and a head. The head is disposed outside of the housing and is for application to dental tissues.

Generally, a head will comprise an array of bristle brushes which are mounted on a base. The base may comprise or function as the mounting component.

The design of the bristle brushes will be such that the head is capable of penetrating the inter-proximal area and in particular the embrasure triangle as well as into deeper periodontal pockets and other dental tissues relevant to the formation of plaque or other dental disease activity.

Generally, the topographical trim of the heads may be pyramidal, conical, V-shaped, dished, domed triangular, square or a combination of these shapes. The angle of the topographical trim may vary from about 40° to about 80° with respect to the base of the head. This angle is critical to allow maximum penetration and activity within the range of naturally occurring inter-proximal areas.

In one preferred embodiment, the head comprises tufts of bristles mounted in the base and made from 600 series nylon. These provide ideal flexibility for general hygiene purposes, sufficient rigidity to remove dental plaque but are sufficiently resilient to provide a gentle massaging effect on the gums. This series of nylon are also more resistant to moisture contamination. Preferably, the length of bristles is between about 5 mm and about 15 mm with the average height of the highest bristles in the peak being about 10 mm.

In this embodiment, the number of bristles per tuft and the number of tufts per unit area of the base are important. In a preferred embodiment, there are 25 bristles per tuft but as required, this may vary from between 15 to 40 bristles per tuft. For this preferred embodiment, the tuft is about 1.5 mm diameter at the base. However, the diameter may vary from between about 1 to about 2 mm. In a particularly preferred embodiment, there is one tuft of bristles per 2 mm squared. However, this may vary from between one tuft per $mm^2$ to one tuft per 4 $mm^2$. This variation is necessary to cater for the wide variation in dental crowding arising from those people with wide gaps between the teeth to those which are crossed, crowded or tilted.

For guidance, the base of a single peaked head is about 7 $mm^2$. However, this may vary from about 5 $mm^2$ to 10 $mm^2$.

In an alternative embodiment, the bristles may be arranged as a single tuft or mass rather than as one or more tufts.

Alternatively, the bristles may be made from any other nylon, plastics material, natural or synthetic material to provide filaments similar to those previously described as bristles.

In a further alternative embodiment, rather than in the form of bristles, the head may comprise a shape formed from a flexible or absorbent material such as rubber, silicone, synthetics plastics materials, felt, condensed paper, cork or wood. These heads may be used to apply medications to affected dental tissues either separately or simultaneously with the removal of dental plaque. Suitable shapes include conical and triangular pyramidal.

As previously mentioned, various components of the handpiece of the invention may be made of metal, plastics materials or mixtures thereof. In general terms, those hand pieces made of plastics will be disposable, that is for single use. In one embodiment formed from plastics materials, the head may be non-removably incorporated in the hand piece. Alternatively, the head may be removable as previously described. Amongst the plastics materials that may be used are polypropylenes, polycarbonates and the like, mixtures thereof or any other suitable plastics materials.

In plastic handpieces of the invention the bearing(s) may exist as simple surface contact areas or any other form of bearing detail. Thus these bearings may be integral or separate from the shaft.

Those hand pieces formed from metal components will generally be reusable, that is they will be capable of cleaning and sterilisation.

For those embodiments formed from both plastics materials and metal components, it is possible to produce embodiments that are either reusable, disposable or both according to choice. However, in producing reusable composite hand pieces it is important to consider the nature of the plastics materials used to ensure that they are capable of being sterilised.

BRIEF DESCRIPTION OF DRAWINGS

FIG. 3 is a sectional view about A—A of FIG. 1;

FIG. 3a is a partial sectional view of an alternate pin and shaft arrangement;

FIG. 3b is a partial sectional view of a further alternate pin and shaft arrangement;

FIG. 4 is a sectional view about B—B of FIG. 1;

MODES FOR CARRYING OUT THE INVENTION

Figure 1:
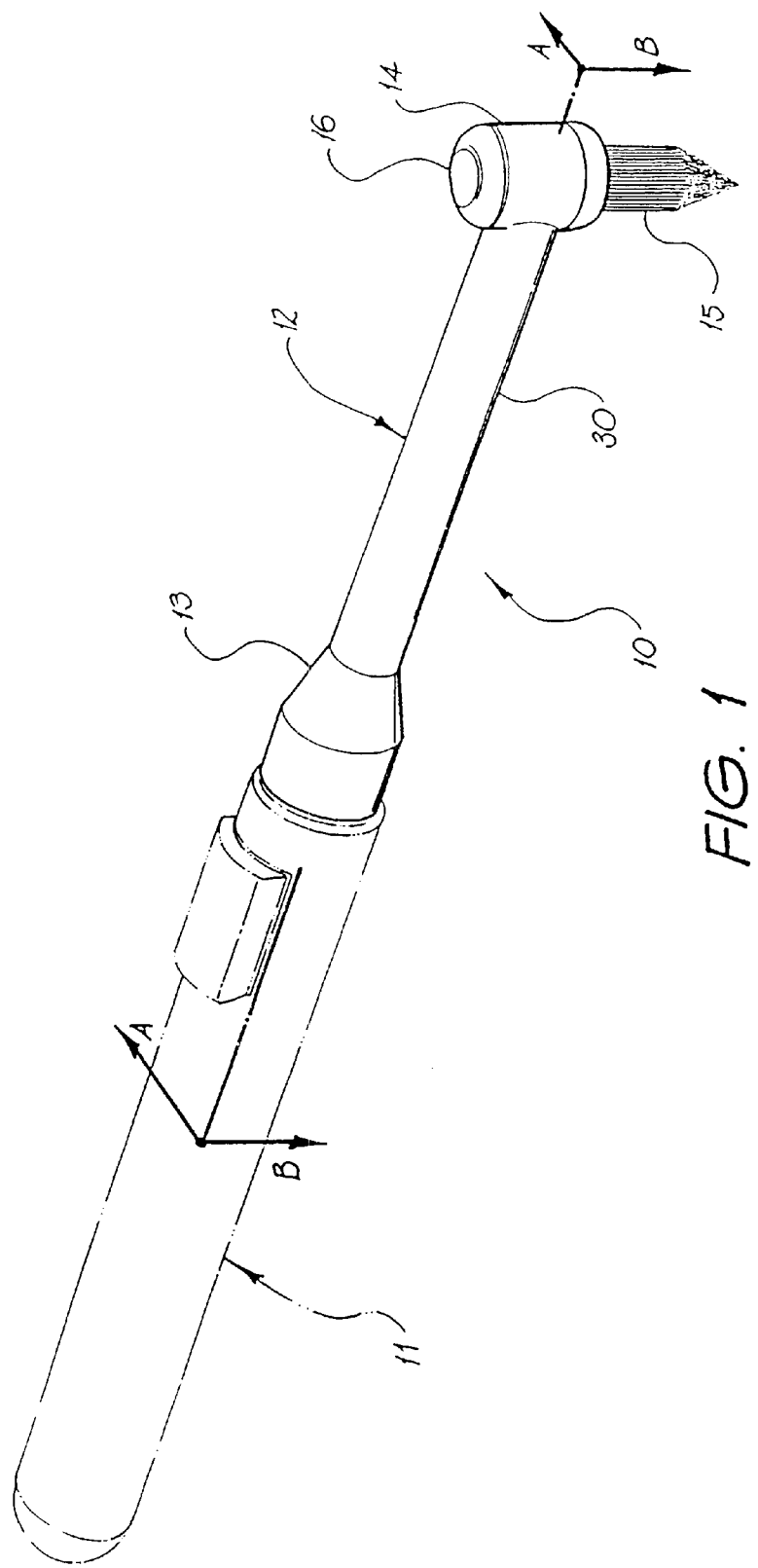
FIG. 1 is a perspective view of a first dental prophylaxis handpiece of the invention.
Figure 2:
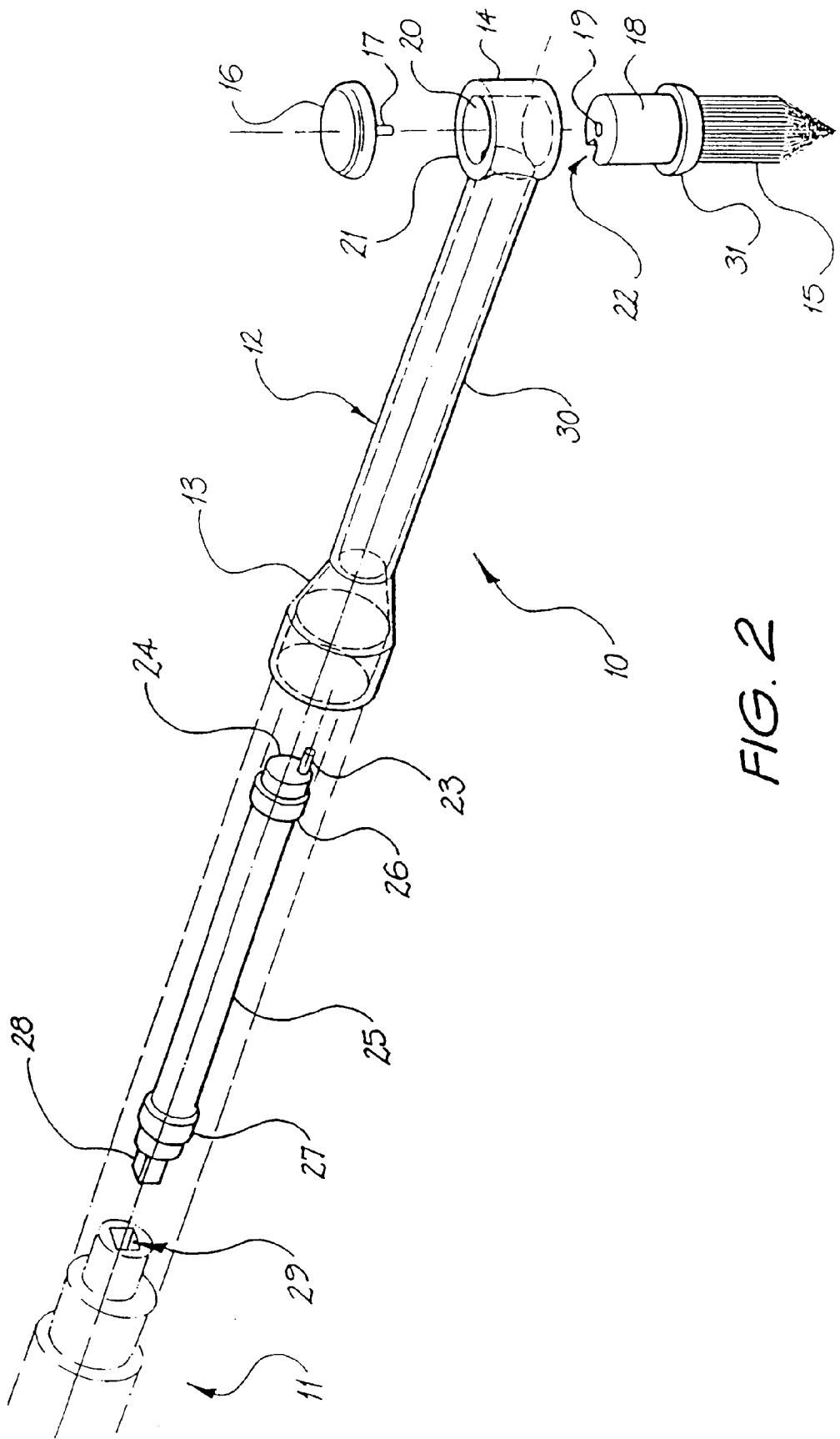
FIG. 2 is an exploded view of the dental prophylaxis handpiece of FIG. 1.

In order to better understand the nature of this invention, a number of embodiments will now be described with reference to the abovementioned drawings.

The dental prophylaxis handpiece 10 comprises a casing 12, one end 13 of which is enlarged to accept a dental handpiece drive 11, whilst the other end includes a substantially cylindrical housing 14.

Between the end 13 and the housing 14, the casing 12 includes a cylindrical portion 30. In this embodiment the casing is moulded in one piece from synthetic plastics material.

Disposed within the casing 12 is a shaft 25 which is circular in cross-section. The shaft 25 is retained within the casing 12 by virtue of journal bearing 27 which is disposed towards the one end of the shaft 25 and journal bearing 26 which is disposed towards the other, housing 14 end.

At the one end of shaft 25 is a connection means which comprises a shank 28. An aperture 29 formed in the dental handpiece drive 11 is dimensioned to accept shank 28 therein.

At the other end of shaft 25 is a pin 23 which extends from the face 24 of the shaft with a longitudinal axis parallel thereto. The pin 23 is offset from the longitudinal axis of the shaft and projects into housing 14.

In the alternative arrangement shown in FIG. 3a, the pin 32 is disposed at an angle of 45° to the longitudinal axis of the shaft 25.

In the further alternative arrangement shown in FIG. 3b, the pin 33 is also disposed at an angle of 45° to the longitudinal axis of the shaft 25. For this arrangement, the pin 33 tapers from its widest dimension where it extends from the face 24 of the shaft to its narrowest dimension distal the face.

Retained within housing 14 is a member comprising a mounting component 18 and a head 15. The mounting component 18 slidingly fits within housing 14 such that pin 23 engages in a groove 22 formed therein. In this embodiment, the groove 22 extends in a plane through the longitudinal axis of the mounting component 18. More particularly, the groove 22 has an external width of 2 mm and an internal width of 1 mm. The depth of the groove 22 is 2 mm.

To retain the member in the housing 14, the mounting component 18 is provided with a circumferential ledge 31 having a diameter greater than the diameter of housing 14. At an upper end of the mounting component 18 is a slot 19 which is adapted to accept a retaining cover 16 having a pin 17. Retaining cover 16 also has a diameter greater than the diameter of housing 14 and when assembled, pin 17 is cemented into slot 19 such that the retaining cover bears on upper surface 21 of housing 14.

Although housing 14 may be disposed with its longitudinal axis at an angle α of between about 90° and about 120° with respect to the longitudinal axis of the shaft 25, in this embodiment the angle is 90°.

Whilst a variety of heads may be used in this invention, head 15 comprises a frustoconical shape formed from tufts of bristles. Whilst the bristles may vary in length from between about 5 mm and about 15 mm, in this embodiment the highest bristles are about 10 mm in length. In this embodiment the bristles are formed from 600 series nylon.

In use, activation of the dental handpiece drive 11 causes shaft 25 to rotate which in turn results in the member comprising the mounting component and head moving in an oscillating arcuate motion.

Figure 10:
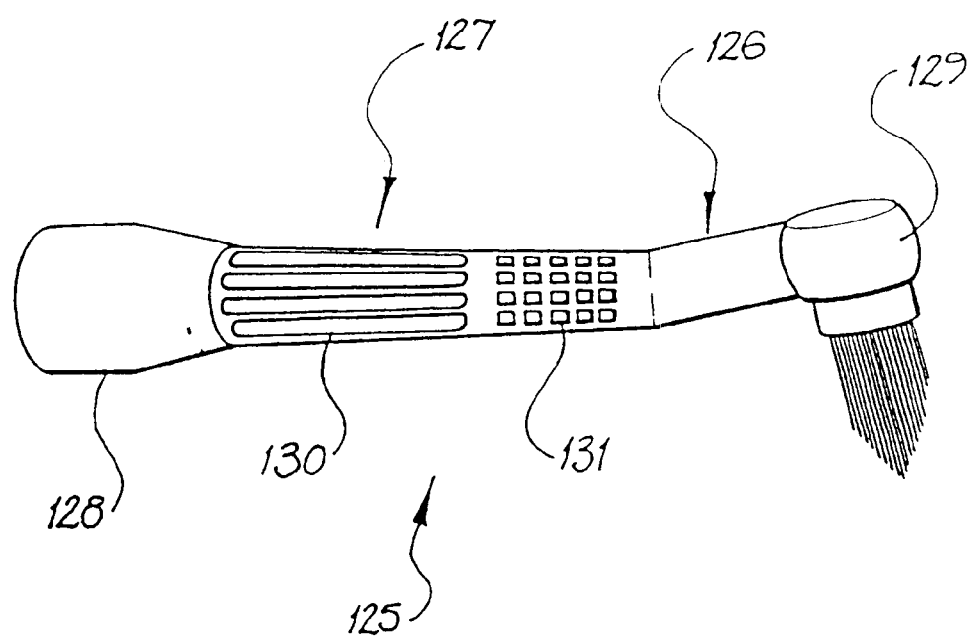
FIG. 10 is a side elevational view of an alternative embodiment of the casing.

In FIG. 10, there is shown an alternative embodiment of the casing for a handpiece of the invention. This handpiece 125 comprises a casing which includes an enlarged portion 128 and a portion 127 tapering from the enlarged portion towards a contra-angled portion 126. Housing 129 is adjacent portion 126.

Along the tapered part of the casing 127, there are a plurality of facets 130 and raised spots 131 so as to enhance gripping.

Figure 5:
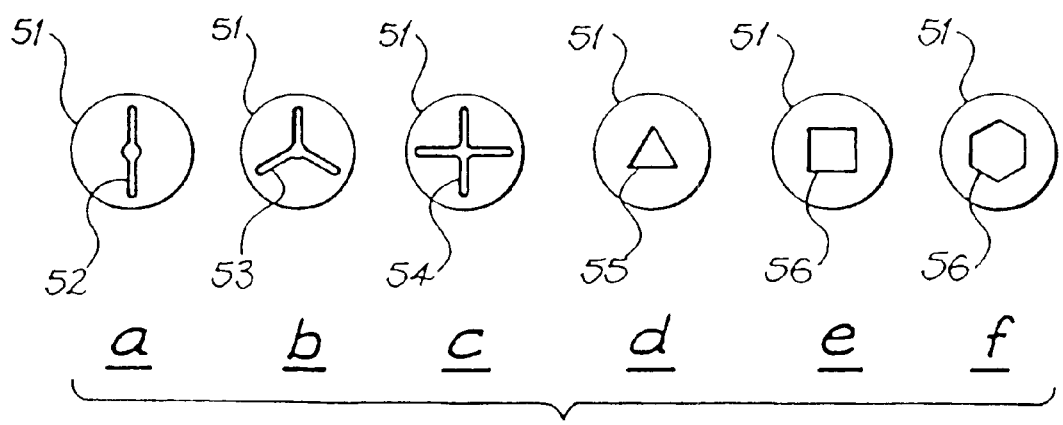
FIG. 5 are end sectional views of six embodiments of one end of the shaft showing various connection means.

Referring now to FIG. 5, there are shown six end sectional views of various connection means to accept a dental handpiece.

In each embodiment, the shaft 51 has a slot shown as 52 in FIG. 5a, 53 in FIG. 5b, 54 in FIG. 5c, 55 in FIG. 5d, 56 in FIG. 5e and 57 in FIG. 5f.

Each of the slots 52, 53, 54, 55, 56 and 57 are shaped so as to accept various standard dental handpiece drives. Thus the handpiece drive would have a shank having a matching shape so as to slidingly fit into a like slot.

It will of course be recognised by a person skilled in the art, that the shaft may be provided with a shank and the handpiece drive provided with a corresponding shape matching slot.

Figure 6:
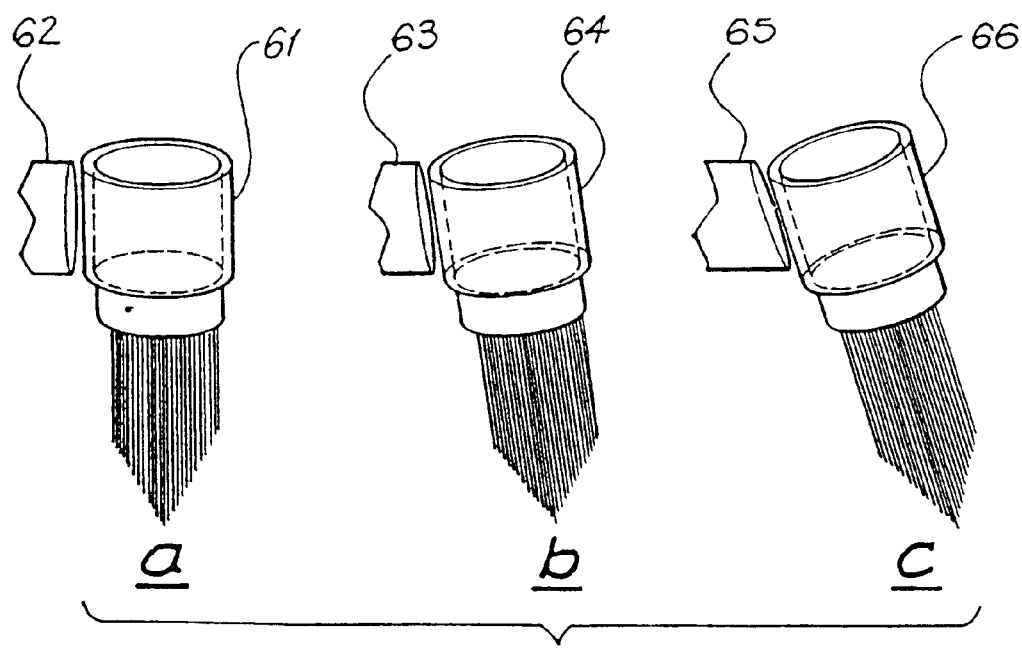
FIG. 6 are partial perspective views of three embodiments of the housing.

In FIG. 6 there are shown three embodiments of the housing in which the housing is disposed at different angles to the casing.

Thus, in FIG. 6a housing 61 has its longitudinal axis at 90° with respect to the longitudinal axis of the casing 62.

In FIG. 6b, the housing has its longitudinal axis at about 100° with respect to the longitudinal axis of the housing 63.

In FIG. 6c, the longitudinal axis of the housing 66 is at an angle of about 120° with respect to the longitudinal axis of the casing 65.

In FIGS. 7a, 7b, 7c, 7f and 7g there are shown five embodiments of the mounting component.

Figure 7:
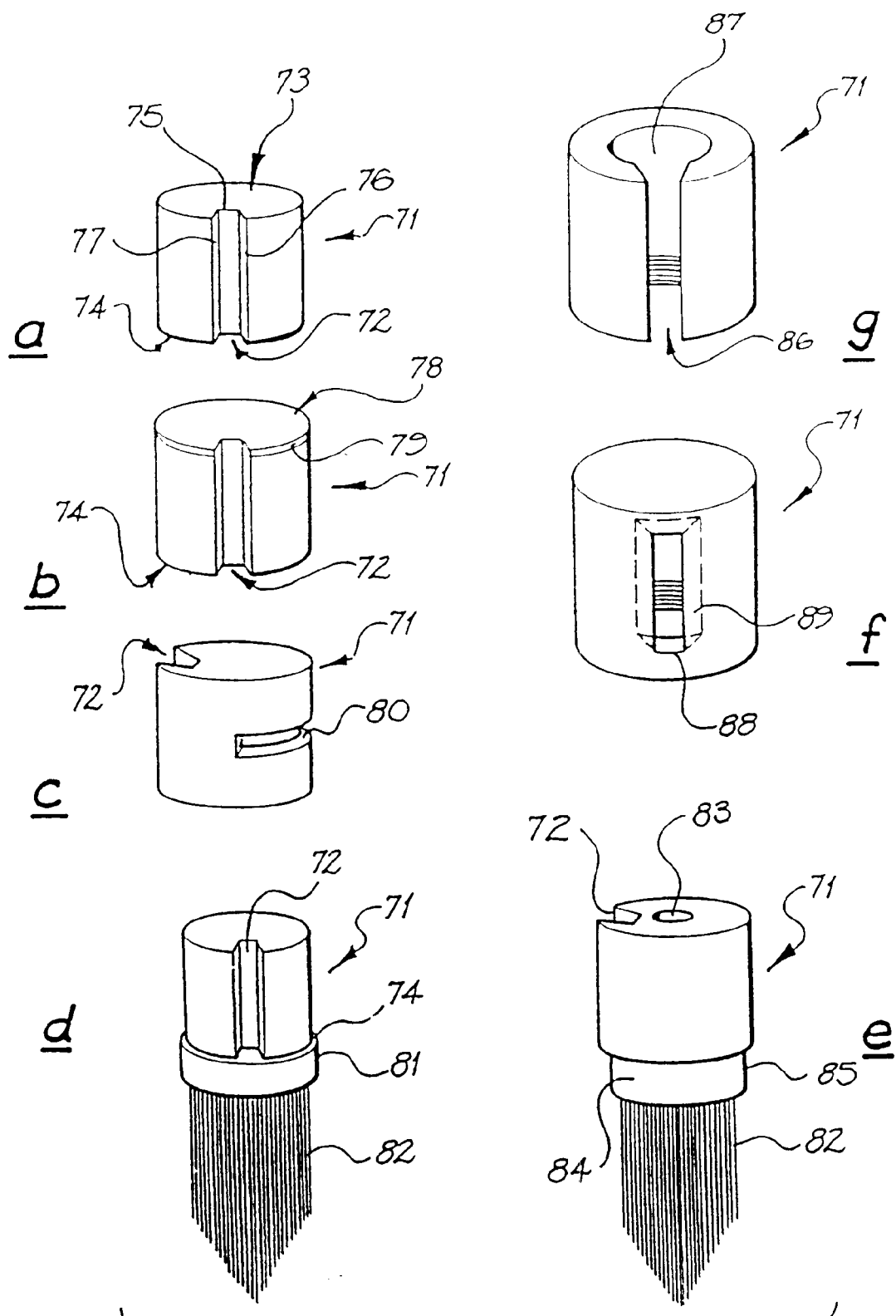
FIGS. 7a, 7b, 7c, 7f and 7g are perspective views of five embodiments of the mounting components, whilst
FIGS. 7d and 7e are perspective views of two embodiments of the member.

Referring to FIG. 7a, the mounting component 71 is substantially cylindrical in shape with a groove 72 extending between a lower face 74 and an upper face 73. Groove 72 has walls 76, 77 which slope inwardly to an inner wall 75 such that the width at the opening of the groove, ie the distance between walls 76 and 77, is greater than the width of the wall 75.

In FIG. 7b, where like parts have been numbered the same as FIG. 7a, in place of upper face 73 there is an enlarged face 78 having a circumferential ledge 79. The ledge 79 is dimensioned such that when placed into a housing, the ledge retains the mounting component therein.

In FIG. 7c, a similar embodiment to that of FIG. 7a is shown with the addition of a second groove 80. This groove 80 is adapted to engage a second pin disposed within the housing so as to retain the member in the housing.

In FIG. 7f, groove 88 has walls 89 which flare inwardly such that the external width of the groove is less than the internal width of the groove.

In FIG. 7g, groove 86 has walls which slope inwardly, such the groove is continuous with a hollow central portion 87 formed in the mounting component 71.

In FIG. 7d there is shown the mounting component of 7a together with a head comprising a base 81 and an array of bristles 82. In this embodiment, the base has been cemented to the mounting component 71.

In FIG. 7e, there is shown another member in which the head comprises, a base 85 and upstanding bristles 82. In this embodiment, the base 85 includes an aperture 84 which when joined with mounting component 71 matches with a corresponding aperture 83 therein. By inserting a sliding latch into apertures 83 and 84, the head is retained on the mounting component. Removal of the latch, allows the head to be readily separated from the mounting component.

Figure 8:
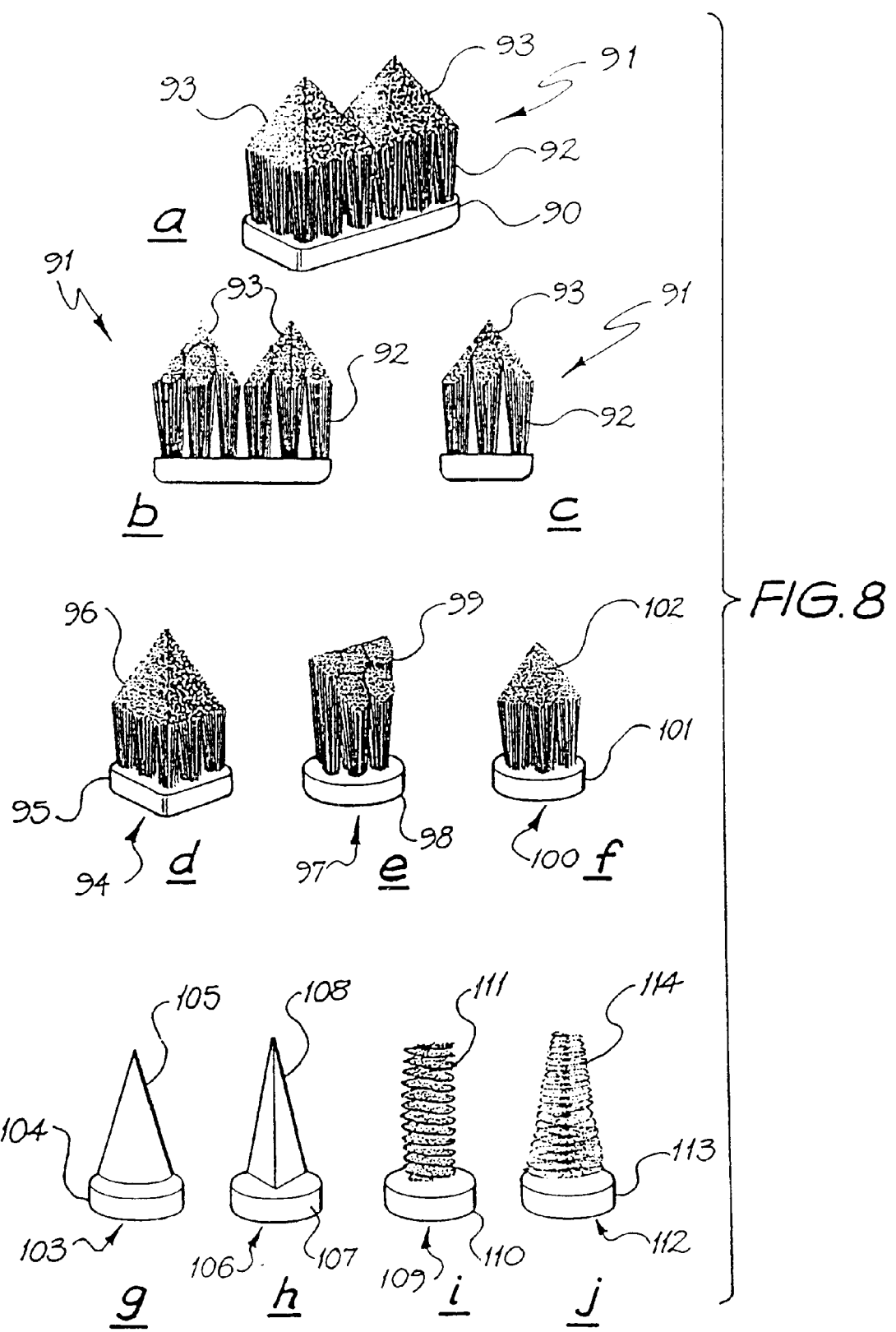
FIGS. 8a, 8b and 8c are respectively perspective, side elevational and end elevational views of one embodiment of a head.
FIGS. 8d–8j are perspective views of seven further embodiments of the head.

In FIGS. 8a, 8b and 8c there is shown a head 91 which comprises an array of upstanding tufts of bristles 92 mounted in a base 91. In this embodiment, the bristles are shaped into two side by side square rectangular shapes.

The bristles are formed from 600 series nylon with the height of the highest bristles in the peak being about 10 mm. There are 25 bristles per tuft with the tufts being about 1.5 mm diameter at the base.

In FIG. 8d there is shown another embodiment of a head 94 comprising a base 95 and upstanding bristles 96. In this case there is a single square pyramidal shape. The specification for the bristles is the same as for the bristles of FIGS. 8a, 8b and 8c.

Similarly, in FIGS. 8e and 8f there are shown a further two embodiments of a head comprising respectively bases 98 and 101 and upstanding bristles 99 and 102.

In the embodiment of FIG. 8e, the bristles are in a V-shape whilst in the case of FIG. 8f, the bristles are in the shape of a cone.

In FIGS. 8g and 8h, alternative embodiments of the head are shown. In FIG. 8g, head 103 comprises a base 104 and a conical portion 105 mounted on the base. The conical portion 105 is formed from silicone and may be used for example for removing plaque.

Similarly, the head 106 of FIG. 8h comprises a base 107 and a triangular pyramidal shape 108. Again, the pyramidal shape 108 is formed from silicone and may be used for removing plaque.

For both of the embodiments shown in FIGS. 8g and 8h, the shaped portions 105 and 108 may be provided with a plurality of ribs, fluting or undulating surface features.

In FIG. 8i, the head 109 comprises a base 110 and a spiral array of bristles 111.

In FIG. 8j, there is shown a second embodiment of a head incorporating a spiral array of bristles 104 mounted in a base 113. In this embodiment the array of bristles has an overall conical shape.

Figure 9:
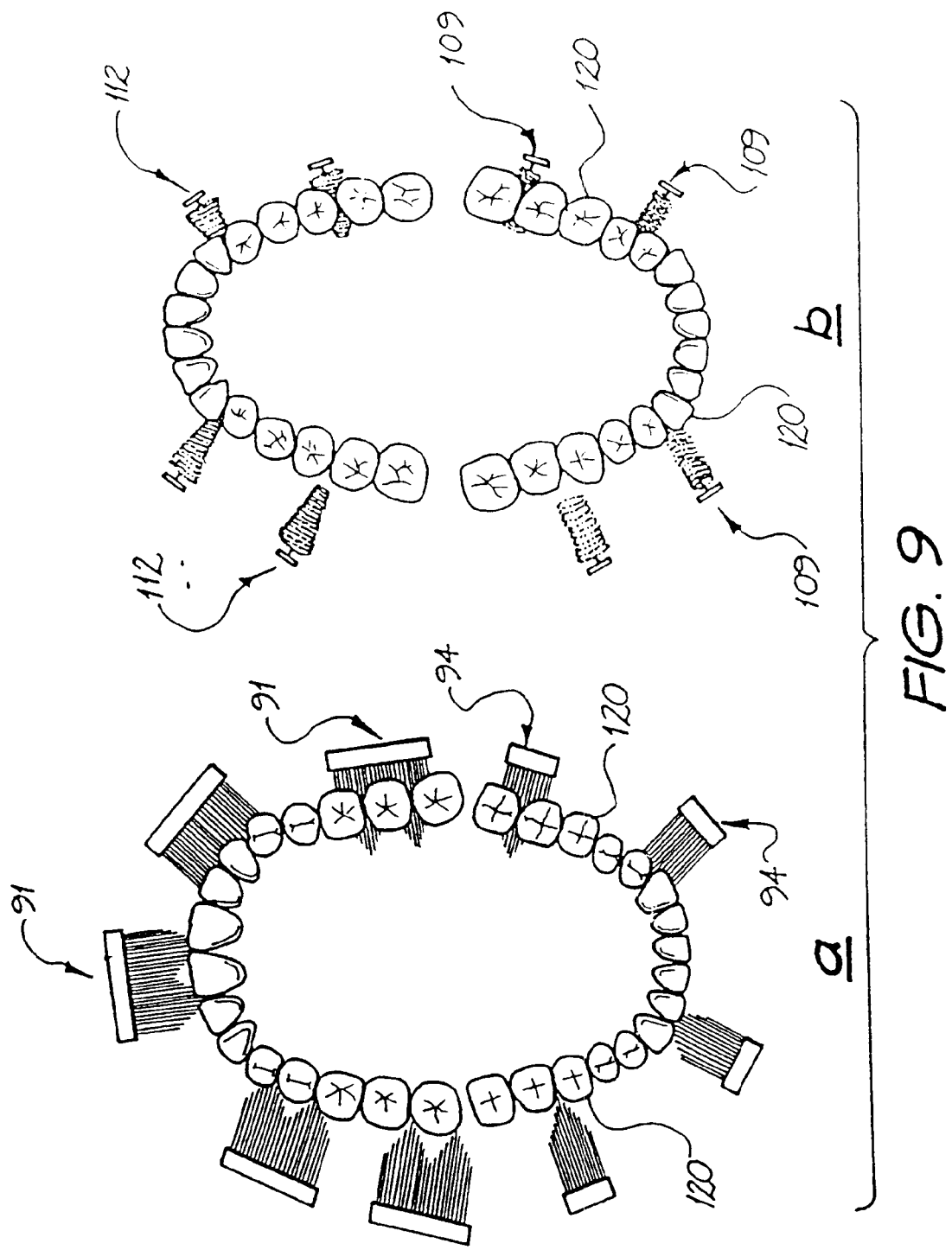
FIG. 9 are schematic views illustrating positioning of various heads in relation to definition.

In FIG. 9a, there is schematically shown the interaction between heads 91, 94 and dentition generally shown as 120.

Similarly in FIG. 9b there is shown the interaction of heads 109 and 112 with dentition generally shown as 120.

In both figures, it is evident that the heads are able to readily access the inter-proximal areas of the dentition.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A dental prophylaxis handpiece comprising a rigid shaft one end of which includes a connection means to accept a dental handpiece drive, the other end of the shaft including a pin with a central longitudinal axis at an angle to a central longitudinal axis of the shaft and extending from a location offset from the central longitudinal axis of the shaft, the pin having its widest dimension on the shaft and tapering away therefrom, one or more bearings disposed about the shaft so as to support the shaft in a casing which extends to encompass the shaft, the casing including a portion at one end to accept the dental handpiece drive and at the other end a housing into which the pin protrudes, the housing being adapted to retain a member comprising a substantially cylindrical mounting component and a head, which head is disposed outside of the housing and is for application to dental tissues, and to permit the pin to engage in a groove in the member in a manner such that operation of the dental handpiece drive causes the shaft to rotate about its central longitudinal axis which in turn imparts an oscillating arcuate motion to the member including the head.

2. A dental prophylaxis handpiece as claimed in claim 1 wherein the connection means comprises a slot in a face of the one end of the shaft.

3. A dental prophylaxis handpiece as claimed in claim 2 wherein the slot is multi-sided in cross-section.

4. A dental prophylaxis handpiece as claimed in claim 2 wherein the slot is arrayed to accept a drive selected from the group consisting of Doriot, E-type, Borden and mid-west.

5. A dental prophylaxis handpiece as claimed in claim 1 wherein the connection means comprises a shank which projects out of a face of the one end of the shaft.

6. A dental prophylaxis handpiece as claimed in claim 1 wherein a first bearing is disposed about the shaft proximate the one end of the shaft and a second bearing disposed about the shaft proximate the other end of the shaft.

7. A dental prophylaxis handpiece as claimed in claim 1 wherein the pin is mounted on a face of the other end of the shaft.

8. A dental prophylaxis handpiece as claimed in claim 7 wherein the pin is located about 1–3 mm from the center of the shaft.

9. A dental prophylaxis handpiece as claimed in 8 wherein the pin has a diameter of between about 1 and 2 mm.

10. A dental prophylaxis handpiece as claimed in 9 wherein the pin has a diameter of about 1.5 mm.

11. A dental prophylaxis handpiece as claimed in claim 8 wherein the pin is located about 2 mm from the center of the shaft.

12. A dental prophylaxis handpiece as claimed in claim 1 wherein the casing adjacent the housing is contra-angled, with the remaining portion of the casing either tapered or substantially cylindrical in shape.

13. A dental prophylaxis handpiece as claimed in claim 12 wherein the shaft comprises two shaft components, a first shaft component including the connection means at one end and a first coupling means at the other end, the first shaft component extending along the longitudinal axis of the substantially cylindrical portion and a second shaft component including a second coupling means at one end and the pin at the other end, the second shaft component extending along the longitudinal axis of the contra-angled portion with the first and the second coupling means being in driving engagement.

14. A dental prophylaxis handpiece as claimed in claim 13 wherein the first coupling means and the second coupling means comprise a crown gear and a pinion gear.

15. A dental prophylaxis handpiece as claimed in claim 14 wherein the longitudinal axis of the housing is at an angle of between about 90° and about 125° with respect to the longitudinal axis of the shaft.

16. A dental prophylaxis handpiece as claimed in claim 15 wherein the groove extends in a curved surface in a plane through the longitudinal axis of the member.

17. A dental prophylaxis handpiece as claimed in claim 15 wherein the groove extends in a curved surface in a plane through the transverse axis of the member.

18. A dental prophylaxis handpiece as claimed in claim 17 wherein the cylindrical portion is in frictional engagement with the inner surface of the housing so as to retain the member.

19. A dental prophylaxis handpiece as claimed in claim 18 wherein a rim is formed on an upper surface of the member, the rim bearing on an upper edge of the housing so as to retain the member in the housing.

20. A dental prophylaxis handpiece as claimed in claim 19 wherein the member includes a second groove which extends transversely to engage a second pin disposed within the housing to retain the member.

21. A dental prophylaxis handpiece as claimed in claim 1 wherein the groove has an external width of about 1 mm to about 3 mm.

22. A dental prophylaxis handpiece as claimed in claim 21 wherein the groove has an internal width of about 0.5 mm to about 2 mm.

23. A dental prophylaxis handpiece as claimed in claim 22 wherein the groove has a depth of about 2 mm.

24. A dental prophylaxis handpiece as claimed in claim 22 wherein the groove has an internal width of about 1 mm.

25. A dental prophylaxis handpiece as claimed in claim 21 wherein the groove has an external width of about 2 mm.

26. A dental prophylaxis handpiece as claimed in claim 1 wherein the head is separably joined to the mounting component.

27. A dental prophylaxis handpiece as claimed in claim 1 wherein the head comprises an array of bristle brushes mounted on a base.

28. A dental prophylaxis handpiece as claimed in claim 1 wherein the head comprises a shape formed from a flexible or absorbent material.

29. A dental prophylaxis handpiece as claimed in claim 28 wherein the head is provided with a plurality of ribs, fluting or undulating surface features.

30. A dental prophylaxis handpiece as claimed in claim 1 wherein the angle of the oscillating arcuate motion of the head is up to 90°.

31. A dental prophylaxis handpiece as claimed in claim 30 wherein the angle of the oscillating arcuate motion of the head is up to 45°.

32. A dental prophylaxis handpiece as claimed in claim 1 wherein the depth of the groove is about 1 to 3 mm.

33. An electrically driven handpiece comprising a rigid shaft one end of which is adapted to drivingly connect to an electric motor, the other end of the shaft including a pin with central longitudinal axis at an angle to a central longitudinal axis of the shaft and from a location offset from the central longitudinal axis of the shaft, the pin having its widest dimension on the shaft and tapering away therefrom, one or more bearings disposed about the shaft so as to support the shaft in a casing which extends to encompass the shaft, the casing including a portion at one end to contain the electric motor and a source of power for the motor and at the other end a housing into which the pin protrudes, the housing being adapted to retain a member comprising a substantially cylindrical mounting component and a head, which head is disposed outside of the housing and is for application to dental tissues, and to permit the pin to engage in a groove in the member in a manner such that operation of the electric motor causes the shaft to rotate about its central longitudinal axis which in turn imparts an oscillating arcuate motion to the member including the head.

34. An electrically driven handpiece as claimed in claim 33 wherein the shaft is directly coupled to the electric motor.

35. An electrically driven handpiece as claimed in claim 33 wherein the shaft is drivingly connected to the electric motor through intermediate gears.

36. An electrically driven handpiece as claimed in claim 33 wherein the pin is mounted on a face of the other end of the shaft.

37. An electrically driven handpiece as claimed in claim 36 wherein the pin is located about 1–3 mm from the center of the shaft.

38. An electrically driven handpiece as claimed in claim 37 wherein the pin has a diameter of between about 1 and 2 mm.

39. An electrically driven handpiece as claimed in claim 38 wherein the pin has a diameter of about 1.5 mm.

40. An electrically driven handpiece as claimed in claim 37 wherein the pin is located about 2 mm from the center of the shaft.

41. An electrically driven handpiece as claimed in claim 33 wherein the casing adjacent the housing is contra-angled, with the remaining portion of the casing either tapered or substantially cylindrical in shape.

42. An electrically driven handpiece as claimed in claim 41 wherein the shaft comprises two shaft components, a first shaft component including the connection means at one end and a first coupling means at the other end, the first shaft component extending along the longitudinal axis of the substantially cylindrical portion and a second shaft component including a second coupling means at one end and the pin at the other end, the second shaft component extending along the longitudinal axis of the contra-angled portion with the first and the second coupling means being in driving engagement.

43. An electrically driven handpiece as claimed in claim 42 wherein the first coupling means and the second coupling means comprise a crown gear and a pinion gear.

44. An electrically driven handpiece as claimed in claim 43 wherein the longitudinal axis of the housing is at an angle of between about 90° and about 125° with respect to the longitudinal axis of the shaft.

45. An electrically driven handpiece as claimed in claim 44 wherein the groove extends in a curved surface in a plane through the longitudinal axis of the member.

46. An electrically driven handpiece as claimed in claim 45 wherein the groove extends in a curved surface in a plane through the transverse axis of the member.

47. An electrically driven handpiece as claimed in claim 46 wherein the cylindrical portion is in frictional engagement with the inner surface of the housing so as to retain the member.

48. An electrically driven handpiece as claimed in claim 47 wherein a rim is formed on an upper surface of the member, the rim bearing on an upper edge of the housing so as to retain the member in the housing.

49. An electrically driven handpiece as claimed in claim 46 wherein the member includes a second groove which extends transversely to engage a second pin disposed within the housing to retain the member.

50. An electrically driven handpiece as claimed in claim 33 wherein the groove has an external width of about 1 mm to about 3 mm.

51. An electrically driven handpiece as claimed in claim 50 wherein the groove has an internal width of about 0.5 mm to about 2 mm.

52. An electrically driven handpiece as claimed in claim 51 wherein the groove has a depth of about 2 mm.

53. An electrically driven handpiece as claimed in claim 51 wherein the groove has an internal width of about 1 mm.

54. An electrically driven handpiece as claimed in claim 50 wherein the groove has an external width of about 2 mm.

55. An electrically driven handpiece as claimed in claim 33 wherein the head is separably joined to the mounting component.

56. An electrically driven handpiece as claimed in claim 33 wherein the head comprises an array of bristle brushes mounted on a base.

57. An electrically driven handpiece as claimed in claim 33 wherein the head comprises a shape formed from a flexible or absorbent.

58. An electrically driven handpiece as claimed in claim 57 wherein the head is provided with a plurality of ribs, fluting or undulating surface features.

59. An electrically driven handpiece as claimed in claim 33 wherein the angle of the oscillating arcuate motion of the head is up to 90°.

60. An electrically driven handpiece as claimed in claim 39 wherein the angle of the oscillating arcuate motion of the head is up to 45°.

61. An electrically driven handpiece as claimed in claim 33 wherein the depth of the groove is about 1 to 3 mm.

* * * * *